United States Patent [19]
Keeney

[11] Patent Number: 6,103,272
[45] Date of Patent: Aug. 15, 2000

[54] COMPOSITIONS FOR STIMULATING HAIR GROWTH, PREVENTING HAIR LOSS, OR MINIMIZING HAIR LOSS, AND METHODS FOR PREPARING AND USING SAME

[76] Inventor: Joseph A. Keeney, Rte. 3, Box 380, Huntington, Tex. 75949

[21] Appl. No.: 09/354,290

[22] Filed: Jul. 15, 1999

[51] Int. Cl.[7] .............................. A31K 33/38; A31K 7/06; A31K 33/34
[52] U.S. Cl. .............................. 424/618; 424/74; 424/630
[58] Field of Search .............................. 514/168; 424/630, 424/618, 401, 70.11, 450, 53, 74; 252/186.29

[56] References Cited

U.S. PATENT DOCUMENTS

| | | | |
|---|---|---|---|
| 4,315,028 | 2/1982 | Scheinberg | 424/290 |
| 5,422,100 | 6/1995 | Eliaz et al. | 424/70.11 |
| 5,437,858 | 8/1995 | Hungerbach et al. | 424/53 |
| 5,514,672 | 5/1996 | Bazzano | 514/168 |
| 5,523,078 | 6/1996 | Baylin | 424/70.1 |
| 5,587,168 | 12/1996 | Vanonou | 424/401 |
| 5,607,693 | 3/1997 | Bonte et al. | 424/450 |
| 5,629,002 | 5/1997 | Weuffen et al. | 424/401 |
| 5,674,510 | 10/1997 | DiTucci | 424/401 |
| 5,932,251 | 8/1999 | Kirkpatric | 424/618 |
| 5,945,032 | 8/1999 | Breitenbach et al. | 252/186.29 |

*Primary Examiner*—William R. A. Jarvis
*Assistant Examiner*—Vickie Kim
*Attorney, Agent, or Firm*—J. M.(Mark) Gilbreth; Gilbreth & Associates P.C.

[57] ABSTRACT

Disclosed are compositions and methods for stimulating hair growth, preventing hair loss or minimizing hair loss. The compositions and methods include topical application and/or an oral administration of colloidal silver.

16 Claims, 3 Drawing Sheets

(3 of 3 Drawing Sheet(s) Filed in Color)

COMPOSITIONS FOR STIMULATING HAIR GROWTH, PREVENTING HAIR LOSS, OR MINIMIZING HAIR LOSS, AND METHODS FOR PREPARING AND USING SAME

BACKGROUND OF THE INVENTION

1. Field of the Invention

The present invention relates to compositions, methods and products for promoting hair growth, slowing hair loss, preventing hair loss, or minimizing hair loss and to methods of using and preparing same. In another aspect, the present invention relates to compositions and products containing colloidal metals for promoting hair growth, slowing hair loss, preventing hair loss, or minimizing hair loss and to methods of using and preparing. In even another aspect the present invention relates to compositions and products administered orally or topically containing colloidal silver for promoting hair growth, slowing hair loss, preventing hair loss, or minimizing hair loss and to methods of using and preparing.

2. Description of the Related Art

Hair loss or alopecia may be caused by a variety of factors including heredity, hormonal deficiencies or imbalances, diet, stress, chemotherapy or aging. The desire to maintain or regain head hair has led to continuing efforts throughout history to discover compositions and methods for stimulating hair growth and for preventing or minimizing hair loss.

Colloidal silver is a suspension of electrically charged microscopic metallic silver. It is known in the prior art as an antimicrobial agent effective against a broad spectrum of pathogens including bacteria, fungi and viruses. It has been used as an antibiotic, water purifier and food preservative. In addition to its use as an anti-microbial agent, claims of the curative properties of colloidal silver include stimulation of healing of injured tissue and bone, tissue regeneration and elimination of old or cancerous cells. Colloidal silver has been administered internally and topically, for example, by injection, as ear and eye drops, or as a topical spray or as an inhalent.

Typically, colloidal silver is produced by inserting pure silver electrodes into distilled or de-ionized water to which sea salt or trace minerals have been added.

There have been many attempts in the prior art to provide effective compositions and methods for promoting hair growth, slowing hair loss, and/or for minimizing or preventing hair loss. However, none of these attempts have utilized colloidal metal or specifically colloidal silver.

U.S. Pat. No. 5,422,100 issued Jun. 6, 1995 to Eliaz et al. discloses methods and products for promoting hair growth, preventing or minimizing hair loss, enhancing or restoring hair color or remelanization and treating other hair and skin afflictions. The methods of the '100 patent include topical applications of the products to the skin or hair follicles being treated. The product of the '100 patent includes a treating agent selected form the class of chemicals consisting of anol, anethole, analogs of the above, polymers of the above, and mixtures of the above with various mixture of these chemicals being found in herb families including umbelliferae, magnoliaceae, labiatae and rutaceae. The '100 invention preferably selects the treatment agent from the class of herbs consisting of Foeniculum vulgares (fennel seed), Pimpinella anisum (anise), Carum carvi (caraway seeds) and mixtures thereof with each other and/or other herbs.

U.S. Pat. No. 5,514,672 issued May 7, 1996 to Bazzano discloses an oral administration or topical application to the skin, hair, and/or hair follicle of effective amounts of retinoid, particularly retinoic acid to increase rate of hair growth, stimulation of hair follicles to produce to produce new hair growth, prolongation of the anagen phase of the hair cycle, and conversion of vellus hair to growth as terminal hair and treatment of alopecia due to organic dysfunction of the hair follicle. The retinoid of the '627 patent may be administered or applied alone or with other adjuctive compounds including vitamins, such as Vitamin $D_3$, hormones, antiandrogens and/or vasodiliators.

U.S. Pat. No. 5,523,078 issued Jun. 4, 1996 to Baylin discloses an aqueous composition for the treatment of hair and scalp which includes a chelating agent, gellan gum, a vitamin precursor, preservative, biotin, a vitamin derivative, γ-linolenic acid, menthol, a liposome, a conditioner, a solubilizer, a conditioner/humectant, folic acid, and a poly amino sugar condensate.

U.S. Pat. No. 5,587,168 issued Dec. 24, 1996 to Vanonou discloses cosmetic preparations containing finely divided solid particles of gold, silver or platinum.

U.S. Pat. No. 5,607,693 issued Mar. 4, 1997 to Bonte et al. discloses a cosmetic or pharmaceutical composition which comprises oxyacanthine, one of its derivatives, one of their cosmetically or pharmaceutically acceptable acid addition salts or an extract of a plant in which it i s present, such as berberis vulgaris or barberry. One particular association is that of oxyacanthine with a saponin for stimulating hair growth, retarding hair loss or combating pruritus.

U.S. Pat. No. 5,629,002 issued May 13, 1997 to Weuffen et al. discloses cosmetic or pharmaceutical preparations for improving the quality and stimulating the growth of hair. The preparations of the '002 patent are based on A) alkali metal, alkaline earth metal and/or ammonium salts of thiocyanic acid in combination with B) at lease one component selected from estrogens, sulfur, sulfide ions, vasodilators, skin-active vitamins, inorganic selenium compounds, amino acids, protein hydrolyzates and carboxylic acids physiologically occurring in the skin or mixtures thereof. The preparations may optionally be in admixture with per se known auxiliary and carrier materials for hair cleaning and hair care agents. A synergistic improvement in the quality of hair and stimulation of hair growth is observed by combining the alkali metal, alkaline earth metal and/or ammonium slats of thiocyanic acid with at least on of the component B materials.

U.S. Pat. No. 5,674,510 issued Oct. 7, 1997 to DiTucci discloses a hair treatment solution capable of acting as a cosmetic, reducing alopecia, eliminating alopecia, increasing hair growth or any combination thereof. The solution of the '510 patent comprises garlic powder, brewer's yeast, grapefruit juice, acetic acid and kelp.

Thus, in spite of the advancements in the prior art, there is a need in the art for compositions for promoting hair growth, slowing hair loss, and for preventing or minimizing hair loss that do not suffer from the deficiencies of the prior art, and for methods of making and using such compositions.

This and other needs in the art will become apparent to those of skill in the art upon review of this specification, including its claims.

SUMMARY OF THE INVENTION

It is an object of the present invention to provide for compositions for promoting hair growth, slowing hair loss, and for preventing or minimizing hair loss that do not suffer from the deficiencies of the prior art, and methods of making and using such compositions.

This and other objects of the present invention will become apparent to those of skill in the art upon review of this specification and claims.

According to one embodiment of the present invention there is provided a topical solution for promoting hair growth which includes a colloidal silver solution. A further embodiment includes a method of making such a topical solution.

According to another embodiment of the present invention, there is provided an oral administration for promoting hair growth which includes a colloidal silver solution. A further embodiment includes a method of making such an oral administration.

According to even another embodiment of the present invention, there is provided a method of promoting hair growth, the method includes applying a topical solution containing colloidal silver to the scalp.

According to still another embodiment of the present invention, there is provided a method of promoting hair growth, the method includes an oral administration a colloidal silver solution.

These and other embodiments of the present invention will become apparent to those of skill in the art upon review of this specification claims.

BRIEF DESCRIPTION OF THE DRAWINGS

This is a notice as required under 37 C.F.R. 1.84(2) that the file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
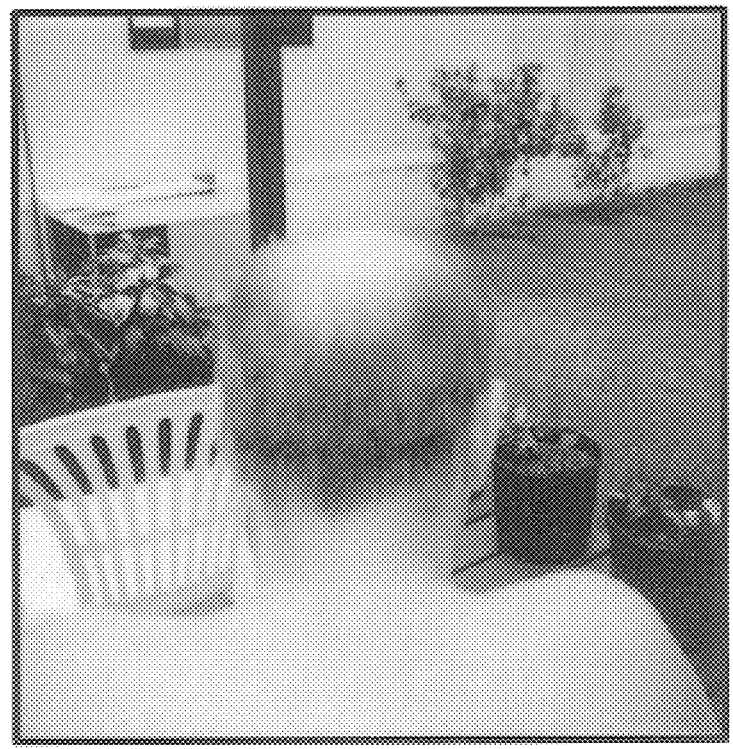
FIG. 1 is a photograph taken at day 63 of treatment illustrating hair growth after about two months of utilizing the compositions and methods of the present invention.

The compositions for stimulating hair growth, preventing hair loss, reducing hair loss, or minimizing hair loss of the present invention include topical applications and/or an oral dosages which include a colloidal metal. Preferably, the colloidal metal may be silver, platinum, gold, copper, zinc or tin. More preferably, the colloidal metal is silver.

Colloidal silver is produced as is known in the art by passing DC current through pure silver electrodes placed into distilled or de-ionized water. For optimum effectiveness, it is important that the water used contain normal amounts of trace minerals. If required, minerals may be added to the distilled or de-ionized water. In addition, saline may be added to enhance conductivity as is known in the art. As one suitable example of the known method and apparatus for the making of colloidal silver, please refer to *Colloidal Silver Making and Using Your Own,* Mark Metcalf, 1998, incorporated herein by reference.

In a first embodiment, the present invention includes a colloidal metal solution to be applied directly to the hair or scalp. Preferably the solution includes colloidal silver in distilled or de-ionized water, at an effective concentration to produce new hair growth, reduce hair loss, and/or to prevent or minimize hair loss. More preferably, sea salt, epson salt and/or trace minerals are added to the distilled or de-ionized water prior to the production of the colloidal silver.

Preferably, the concentration of colloidal metal in the water is between about 1 parts per million ($\mu$g/ml) to about 1000 $\mu$g/ml. More preferably, the concentration of colloidal metal is between about 1 $\mu$g/ml to about 750 $\mu$g/ml, even more preferably, between about 50 $\mu$g/ml to about 500 $\mu$g/ml and most preferably, between about 250 $\mu$g/ml and about 350 $\mu$g/ml.

In the method of making, the topical ingredients are mixed together by methods and apparatus as is known in the art. To use, the water containing the colloidal silver is applied directly to the area to be treated. The area to be treated may be wetted with the colloidal silver solution, or the colloidal silver solution may be applied to the area with a cloth or cotton. Preferably, the area to be treated is wetted with the colloidal silver solution to prevent damage to new hair growth by rubbing. After application of the colloidal silver solution, the treated area is then allowed to air dry.

In a second embodiment, the topical application includes a colloidal metal solution and aloe vera. The colloidal metal solution is a colloidal metal, preferably colloidal silver, in distilled or in de-ionized water. Preferably the solution includes colloidal silver at an effective concentration to produce new hair growth, reduce hair loss, and/or to prevent or minimize hair loss. More preferably, the colloidal silver is at a concentration between about 1 parts per million ($\mu$g/ml) to about 1000 $\mu$g/ml. Even more preferably, the concentration of colloidal silver is between about 20 $\mu$g/ml to about 750 $\mu$g/ml, still more preferably, between about 50 $\mu$g/ml to about 500 $\mu$g/ml and most preferably between about 100 $\mu$g/ml to about 200 $\mu$g/ml. As described above, the colloidal metal solution may be prepared with the addition of sea salt or trace minerals.

The aloe vera may be any aloe vera currently available, but is preferably an aloe vera gel that is at least about 99% pure. More preferably, the aloe vera is an aloe vera gel containing plant and herbs as currently available from Southwest Sunshine Products located in Queen Creek, Ariz. Not wishing to be limited by theory, the inventor believes that one or more of the skin healing, cleaning and protecting plant and herbal components of the aloe vera gel available from Southwest Sunshine products, namely allantoin, arnica flowers, comfrey leaves, horsetail herbal extract, jojoba, collogen, elastin, saponins, chamomile flowers, elkweed, jaborandi leaves, napca and rosemary leaves, enhance the effectiveness of the topical applications of colloidal metal of the present invention. Accordingly, it is believed that one or more of these plant and herbal components may be added as necessary or desired.

Any suitable relative amounts of the colloidal metal solution and aloe vera may be utilized in the present invention provided that the desired stimulation of hair growth, prevention of hair loss or minimization or reduction of hair loss are achieved. Preferably, the topical application includes between about 5% to about 50% by volume colloidal metal solution and between about 50% to about 95% aloe vera by volume, based on the total volume of metal solution and aloe vera, and more preferably between about 15% to about 25% by volume colloidal metal and between about 75% to about 85% aloe vera by volume.

As a alternative to mixing the colloidal silver solution with the aloe vera, the silver electrodes may be inserted directly into the aloe vera gel so that colloidal silver is produced directly in the gel until an effective concentration of colloidal silver, as described above, is obtained.

To use, the colloidal metal aloe vera mixture is applied directly to the area to be treated using application methods as are known in the art.

A third embodiment of the topical application of the present invention includes a colloidal metal solution, aloe vera and at least one of the following items selected from the group consisting of vitamins, iodine, ginseng, and/or vinegar. The colloidal metal solution and aloe vera are as described above in the second embodiment. The vitamins, preferably vitamin A, vitamin E and vitamin D, the iodine, and the vinegar are as currently available in the market. The iodine is preferably BETADINE available from Prude Fredrickson in Norwalk, Conn., and the vinegar is preferably apple cider vinegar available from Heinz in Pittsburgh, Pa.

Any suitable relative amounts of the colloidal metal solution, aloe vera, vitamins and/or vinegar may be utilized in the present embodiment provided that the desired stimulation of hair growth, prevention of hair loss or minimization of hair loss are achieved. The relative amounts of colloidal metal solution and aloe vera are as described above in the second embodiment. Preferably, the third embodiment includes Vitamin A at a concentration of between about 10,000 I.U. and about 50,000 I.U, Vitamin E at a concentration of between about 1000 I.U. and about 8000 I.U. and vinegar at a concentration of about 1% to about 5% by total volume of the colloidal metal solution. Most preferably, the embodiment includes about 3% to about 4% vinegar by volume, about 40,000 I.U. Vitamin A and about 5000 I.U. Vitamin E.

In addition to the above ingredients, the topical applications of the present invention may also contain additions of one or more herbs and other plants in known beneficial amounts. For example, one or more additional rosemary leaves, comfrey leaves, jaborandi leaves, chamomile flowers, arnica flowers, watercress, saponins, and allantoin may be added as desired.

To use, the colloidal metal aloe vera mixture containing vitamins, vinegar, herbs and/or other plants, is applied directly to the area to be treated.

The inventor also believes an oral administration of colloidal metal prepared as described above in distilled or de-ionized water is beneficial in promoting new hair growth and preventing or minimizing hair loss. Preferably, the administration includes a daily dosage of colloidal silver. Preferably, the dosage includes between about 1 teaspoon and about 64 oz of colloidal silver in distilled or de-ionized water at a concentration of about 1 $\mu$g/ml to about 500 $\mu$g/ml. More preferably, the dosage includes between about 1 oz and 20 oz of colloidal silver in distilled or de-ionized water at a concentration of bout 50 $\mu$g/ml to about 350 $\mu$g/ml. Even more preferably, the daily dosage includes between about 4 oz and 20 oz of colloidal silver in distilled or de-ionized water at a concentration of bout 100 $\mu$g/ml to about 250 $\mu$g/ml.

The method of making the topical or oral administration described above, include mixing the ingredients using methods and apparatus as are known to those skilled in the art.

In addition to the above oral administration and/or the above topical, the inventor believes that the following booster combination, taken orally and concurrently, enhances the ability of present invention to stimulate new hair growth and prevent or minimize hair loss. This booster combination includes vinegar, water and honey. Preferably, the vinegar is apple cider vinegar. The booster combination may also include one or more of kelp, alfalfa, Vitamins A and E, iron, ginseng, and acidophilus apple pectin, silica, or a multivitamin as currently available, in tablet or other forms, in the market.

Any suitable relative amounts of vinegar, water and honey may be utilized provided that the desired enhancement of the stimulation of hair growth, reduction of hair loss, prevention of hair loss or minimization of hair loss are achieved. Preferably, The booster composition contains about 5% to about 95% of total volume of vinegar and more preferably contains about 20% to about 40% of total volume vinegar. Preferably, the booster combination includes between about 200 mg and about 700 mg Norwegian kelp, between about 5000 I.U. and about 10000 I.U. Vitamin A, between about 500 I.U. and about 1500 I.U. Vitamin E, between about 10 mg to about 100 mg iron, between about 50 mg and about 150 mg GINSANA and between about 50 g and about 150 mg acidophilus apple pectin.

In a most preferred embodiment, the methods of the present invention includes utilizing a combination of an oral administration of and a topical administration of the compositions of the present invention along with the booster composition all as described above.

EXAMPLES

The following examples are provided merely to illustrate the present invention, and is not intended to limit the scope of the claims.

Example 1

As a non-limiting example, the preferred topical contains between about 250 $\mu$g/ml and about 350 $\mu$g/ml colloidal silver prepared from commercially available ABITA SPRINGS distilled water. ABITA SPRINGS is located in Abita Springs, La. About 8 oz of ABITA SPRINGS distilled water and 1 drop saline solution is heated to about 150° F. with the current passing through the silver electrodes for about 45 minutes to produce a brown colored colloidal. The saline solution contains about ½ teaspoon in about 2 oz of distilled water as described in *Colloidal Silver Making and Using Your Own*, p. 8, Mark Metcalf, 1998.

Example 2

As a non-limiting example, the preferred drink contains about 100 $\mu$g/ml to about 250 $\mu$g/ml colloidal silver prepared from DANNON natural spring water. DANNON is located in Pedmont, Quebec Canada. The DANNON water analysis indicates trace materials including bicarbonate, calcium, chlorine, fluoride, magnesium, nitrate, potassium, sodium, sulfate, and dissolved solids and has a pH of around 7. About 16 oz of DANNON water is heated to about 120° F. with the current passing through the silver electrodes for about 8 minutes to produce a silver colored colloidal.

Example 3

As a non-limiting example, the booster includes about 1 teaspoon apple cider vinegar, 1 oz water and 1 oz honey taken with a multivitamin and 8000 I.U. Vitamin A and 1000

I.U. Vitamin E as available from Spring Valley, taken once daily. In addition, the booster may include 650 mg Alfafa taken twice daily, 110 mg Acidophillus Rexal, as avialable from Rexall Sundown located in Boco Raton, Fla., taken once daily, 550 mg Kelp, as available from Norwegian Kelp Caps located in Glendale Heights, Ill., taken twice daily, 27 mg iron taken once daily, SILICEA 6x, available from P&S Lab located in Los Angelos, California, taken once daily, and 100 mg GINSANA taken once daily.

Example Trial

This example documents the observations of the inventor, a user of the compositions and methods of the present invention.

Day 1. Begin oral administration of 1 teaspoon of 5 μg/ml colloidal silver prepared in distilled water to which 1 drop of sea salt solution, containing ½ teaspoon sea salt in 2 oz of distilled water, had been added.

Day 46. Have continued March 15 dosage now for 46 consecutive days. Begin use of aloe vera gel with herb and plant mixture as available from Southwest Sunshine Herbal Skin Care Products.

Day 49. Began noticing very fine and small hair follicles on area of scalp visible with magnifying glass. Continue March 15 oral dosage, applying aloe vera gel with herbs once at night and begin use of 5 μg/ml colloidal silver as a topical applied with cotton once in morning.

Day 56. Hair follicles visible with naked eye with more follicles being visible with magnifying glass. All growth appearing at base of the back of the head. Increase oral dosage to 1 oz of 40 μg/ml colloidal silver in distilled water. Begin application of 40 μg/ml colloidal silver as a topical applied with cotton once in morning. Continue application of aloe vera gel with herbs once at night.

Day 63. Referring now to FIG. 1, there is shown a photograph illustrating hair growth after about 2 months of utilizing the compositions and methods of the present invention. Hair which first appeared on May 2 are now about ¼ inch long and white to blonde in color. Follicles seem to be appearing in a pattern moving in and upward from the base of the neck. Continue oral dosage of 1 oz of 40 μg/ml colloidal silver in distilled water. Begin application of 300 μg/ml colloidal silver in distilled water as a topical applied with cotton once a day alternating daily with use of aloe vera gel with herbs.

Day 82. Hair continues to grow inward around hairline with new hair beginning to appear on the sides of head. Continue oral dosage of 1 oz of 40 μg/ml colloidal silver in distilled water, and alternate daily applications of 300 μg/ml colloidal silver in distilled water as a topical applied with cotton and of aloe vera gel with herbs.

Day 125. Hair filling in at base faster with hair on sides growing inward and upward. Skin on top of head is becoming less dry and rough. New hairs beginning to itch as they break through skin on scalp. Begin oral dosage of 4 oz of 40 μg/ml colloidal silver in distilled water. Continue alternate daily applications of 300 μg/ml colloidal silver in distilled water as a topical applied with cotton and of aloe vera gel with herbs.

Day 135. Hair growth continuing upward and inward. New growth has begun around hairline on top of head. Small new growth is coming out around early hair and across scalp. Continue oral dosage of 4 oz of 40 μg/ml colloidal silver in distilled water, and alternate daily applications of 300 μg/ml colloidal silver in distilled water as a topical applied with cotton and of aloe vera gel with herbs.

Figure 2:
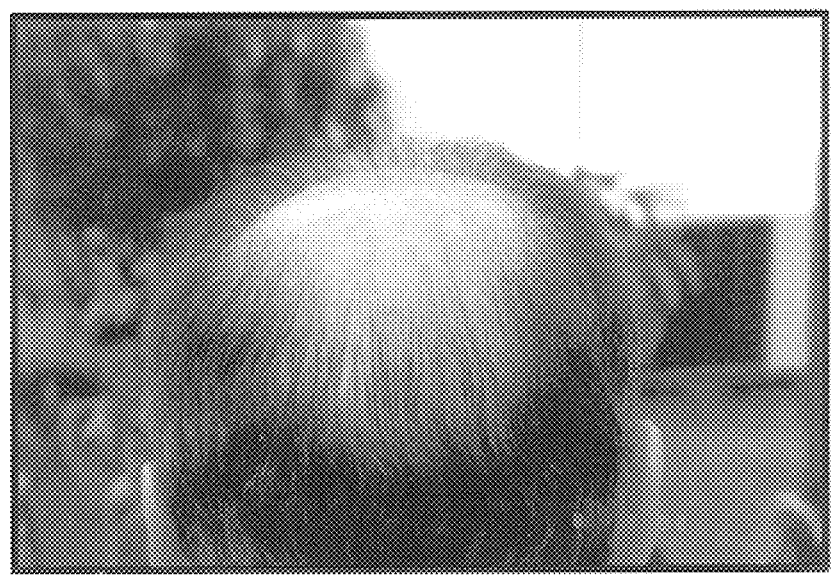
FIG. 2 is a photograph taken at day 148 of treatment illustrating hair growth after about five months of utilizing the compositions and methods of the present invention.

Day 148. Referring now to FIG. 2, there is shown a photograph illustrating hair growth after about 5 months of utilizing the compositions and methods of the present invention. Hair growth continues inward at top of base. Itching and tickling sensation occurs when applying topical mix. Sunlight produces same sensation. Begin oral dosage of 6 oz of 40 μg/ml colloidal silver in distilled water. Continue alternate daily applications of 300 μg/ml colloidal silver in distilled water as a topical applied with cotton and of aloe vera gel with herbs.

Day 164. Hair growth continues upward to top with new growth on top moving downward. In some parts of scalp, small red dots appear before hair breaks through. Itching and tickling sensation have increased. Small amounts of young hair come off on cotton when dabbing on the topical solution. Continue oral dosage of 6 oz of 40 μg/ml colloidal silver in distilled water. Begin application of 300 μg/ml colloidal silver in distilled water by wetting hair with solution. Continue alternate daily applications of topical and aloe vera with herbs.

Day 179. Hair growing upward and inward moving towards crown. Itching and tickling sensation occurring all over scalp. New hairs still coming in with small hairs appearing in crown area. Continue oral dosage of 6 oz of 40 μg/ml colloidal silver in distilled water and alternate daily application of 300 μg/ml colloidal silver in distilled water by wetting hair with solution and applications of aloe vera with herbs. Begin use of cocoa butter with the aloe vera with herbs.

Day 194. Hair continues to grow on all areas of head with new hair mixing with old. Itching and tickling sensation continues. Continue oral dosage of 6 oz of 40 μg/ml colloidal silver in distilled water and alternate daily application of 300 μg/ml colloidal silver in distilled water by wetting hair with solution and applications of aloe vera with herbs.

Day 209. Hair continues to grow on all areas of head. New hair breaking through increasingly thicker and is now beard like. Itching and tickling sensation almost constant. Continue oral dosage of 6 oz of 40 μg/ml colloidal silver in distilled water and alternate daily application of 300 μg/ml colloidal silver in distilled water by wetting hair with solution and applications of aloe vera with herbs.

Day 223. Hair continues to grow on all areas of head. Begin oral dosage of 6 oz of 80 μg/ml colloidal silver in distilled water and alternate daily application of 300 μg/ml colloidal silver in distilled water by wetting hair with solution and applications of aloe vera with herbs.

Figure 3:
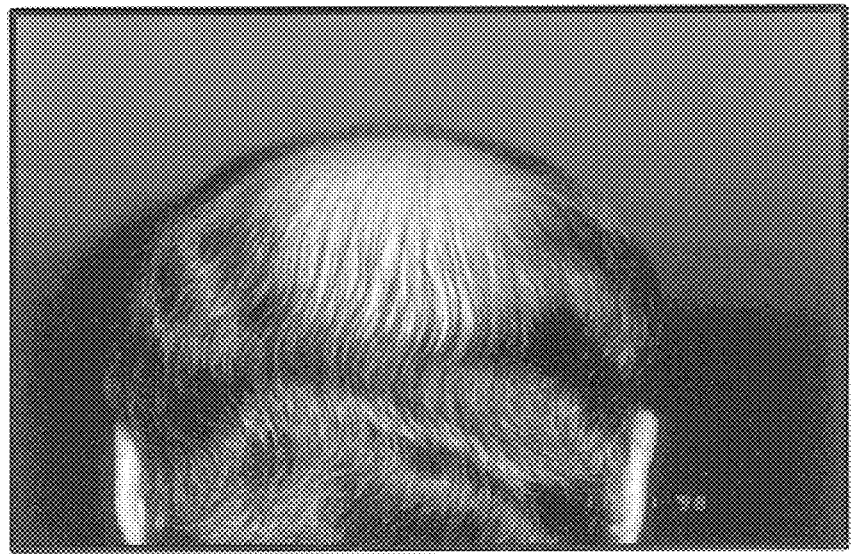
FIG. 3 is a photograph taken at day 232 of treatment illustrating hair growth after amount eight months of utilizing the compositions and methods of the present invention.

Day 232. Referring now to FIG. 3. there is shown a photograph illustrating hair growth after about 8 months of utilizing the compositions and methods of the present invention., hair still growing with new breakout. Itching and tickling has slowed down. Hair has filled in over all balding area now. Continue oral daily dosage of 6 oz of 80 μg/ml colloidal silver and alternate daily application of 300 μg/ml colloidal silver in distilled water by wetting hair with solution and applications of aloe vera with herbs.

Days 245–262. Hair continues growing in. Continue oral daily dosage of 6 oz of 80 μg/ml colloidal silver and alternate daily application of 300 μg/ml colloidal silver in distilled water by wetting hair with solution and applications of aloe vera with herbs.

Figure 4:
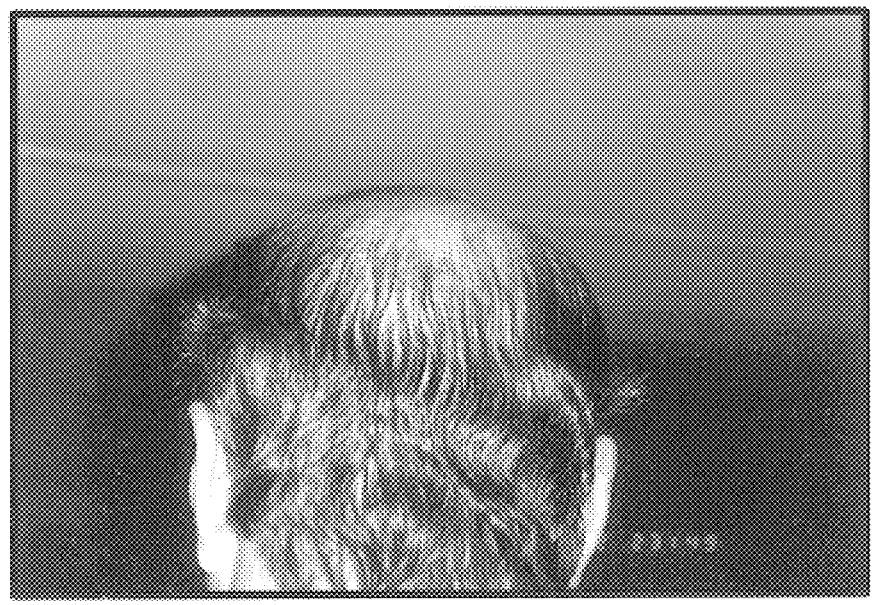
FIG. 4 is a photograph taken at day 279 of treatment illustrating hair growth after about nine months of utilizing the compositions and methods of the present invention.

Day 279. Referring now to FIG. 4 there is shown a photograph illustrating hair growth after about 9 months of utilizing the compositions and methods of the present invention., new hair is still coming in over all parts of head. Begin use of Apolliinaris mineral water for silver colored colloidal drink taking oral dosage of 6 oz of 160 μg/ml. Continue alternate daily application of 300 μg/ml colloidal silver in distilled water by wetting hair with solution and applications of aloe vera with herbs.

Figure 5:
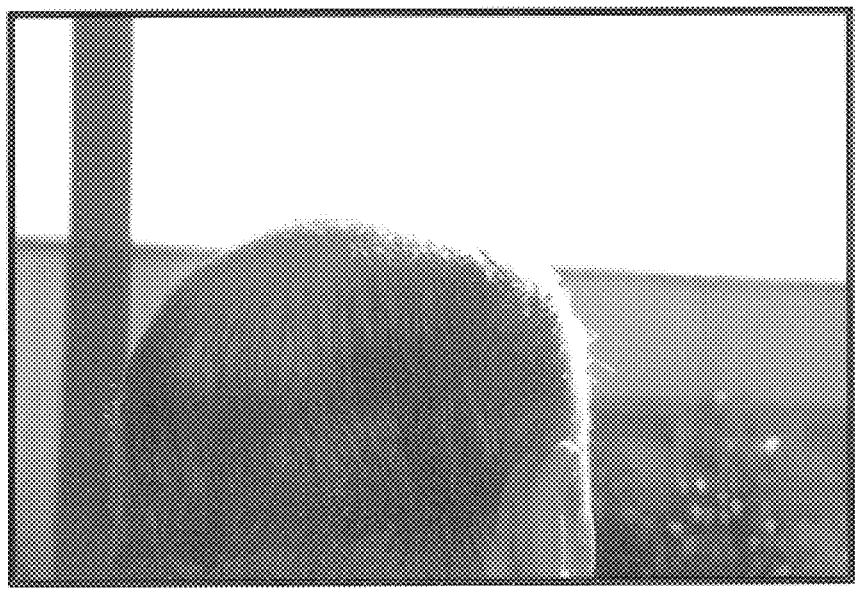
FIG. 5 is a photograph taken at day 333 of treatment illustrating hair growth after about eleven months of utilizing the compositions and methods of the present invention.

Day 333. Referring now to FIG. 5, there is shown a photograph illustrating hair growth after about 11 months of utilizing the compositions and methods of the present invention. Hair still growing with lots of new breakout all over heard. Begin using Silicea 6× with 4 tablets daily dissolved in spring water. Temple area of scalp beginning to grow out nicely.

Figure 6:
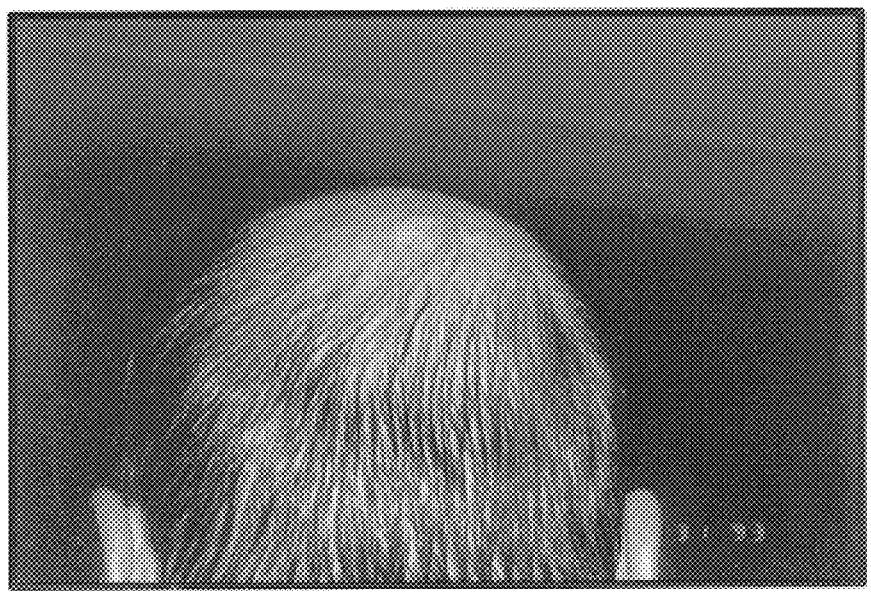
FIG. 6 is a photograph taken about at day 362 of treatment illustrating hair growth after about one year of utilizing the compositions and methods of the present invention.

Referring now to FIG. 6, there is shown a photograph taken about Day 362, illustrating hair growth after about 1 year of utilizing the compositions and methods of the present invention.

While not wishing to be limited by theory, the inventor believes that the colloidal silver drink of the present invention detoxifies and cleanses cells throughout the body removing by-products and balancing the body's pH to the alkaline side. The inventor also believes that the topical solution of colloidal silver cleanses and removes pollutants that attach themselves to the scalp providing a layered cleansing effect. In addition, the inventor believes that the aloe and herb topical mixture, when charged with silver, promotes an even more powerful cleansing while also providing a healing, softening and protective agent to assist in the regrowth of cells and hair. For a reference on the healing ability of herbs, please see *The Healing Herbs ultimate Guide,* Michael Castleman, 1991 Bantum Books, incorporated herein by reference. The inventor further believes that his use of the colloidal silver, aloe vera, herbs and supplements in conjunction has resulted in his hair regrowth on the top back and in the temple area of his scalp.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

I claim:

1. A topical solution for promoting hair growth, the solution consisting essentially of between about 1 and about 1000 μg/ml colloidal silver.

2. The topical solution of claim 1 wherein the colloidal silver solution further comprises distilled water.

3. The topical solution of claim 1 further comprising aloe vera gel.

4. The topical solution of claim 3 wherein the aloe vera gel further comprising a least one additive selected from the group consiting of allantoin, arnica flowers, comfrey leaves, horsetail herbal extract, jojoba, collogen, elastin, saponins, chamomile flowers, elkweed, jaborandi leaves, napca and rosemary leaves.

5. An oral administration for promoting hair growth, the oral administration consisting essentially of a colloidal silver concentration between about 1 μg/ml and about 500 μg/ml.

6. The oral administration of claim 5 wherein the colloidal silver solution further comprises between about 1 teaspoon and about 64 oz of water.

7. The oral administration of claim 6 wherein the water comprises distilled water and an additive selected from the group consisting of sea salt, epson salt, trace minerals, and a combination thereof, is added to the distilled water prior to the production of the colloidal silver solution.

8. The oral administration of claim 5 further comprising vinegar in an effective amount to aid in the stimulation of hair growth.

9. A method of promoting hair growth, the method comprising:

applying a topical solution consisting essentially of colloidal silver to the scalp, the topical solution comprising between about 1 and about 1000 μg/ml colloidal silver.

10. The method of claim 9 wherein the topical solution further comprises distilled water.

11. The method of claim 9 wherein the topical solution further comprises iodine.

12. The method of claim 9, further comprises the step of (b) applying aloe vera gel to the scalp.

13. The method of claim 12 wherein the aloe vera gel further comprising an additive selected from the group consisting of allantoin, arnica flowers, comfrey leaves, horsetail herbal extract, jojoba, collogen, elastin, saponins, chamomile flowers, elkweed, jaborandi leaves, napca, rosemary leaves and a combination thereof.

14. The method of claim 9 further comprising the step of (c) administering orally a colloidal solution consiting essentially of silver.

15. The method of claim 14 wherein the colloidal silver solution comprises between about 1 teaspoon and about 64 oz of distilled water with a colloidal silver concentration between about 1 μg/ml and about 500 μg/ml.

16. The method of claim 8 further comprising the step of (d) administering orally a booster selected from the group consisting of vinegar, honey, multivitamin tablet, Vitamin A, Vitamin E, Alfafa, Acidophillus Rexal, Kelp, silca, ginseng, and a combination thereof.

* * * * *